United States Patent
Yamka et al.

(10) Patent No.: US 9,011,900 B2
(45) Date of Patent: *Apr. 21, 2015

(54) COMPOSITIONS INCLUDING PYRUVATE FOR COMPANION ANIMALS AND METHODS OF USE THEREOF

(75) Inventors: Ryan Michael Yamka, Succasunna, NJ (US); Nolan Zebulon Frantz, Andover, NJ (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/519,803

(22) PCT Filed: Dec. 22, 2010

(86) PCT No.: PCT/US2010/061875
§ 371 (c)(1),
(2), (4) Date: Jun. 28, 2012

(87) PCT Pub. No.: WO2011/082081
PCT Pub. Date: Jul. 7, 2011

(65) Prior Publication Data
US 2012/0309829 A1  Dec. 6, 2012

Related U.S. Application Data

(60) Provisional application No. 61/290,780, filed on Dec. 29, 2009.

(51) Int. Cl.
*A61K 31/19* (2006.01)
*A23K 1/16* (2006.01)
*A61P 3/04* (2006.01)
*A23K 1/18* (2006.01)

(52) U.S. Cl.
CPC ............. *A23K 1/1846* (2013.01); *A23K 1/1609* (2013.01); *A61K 31/19* (2013.01)

(58) Field of Classification Search
CPC .... A23K 1/1609; A23K 1/1846; A61K 31/19
USPC .................. 514/557; 424/442; 426/2
See application file for complete search history.

(56) References Cited

U.S. PATENT DOCUMENTS

| | | | |
|---|---|---|---|
| 3,202,514 | A | 8/1965 | Burgess et al. |
| 4,997,671 | A | 3/1991 | Spanier |
| 4,997,672 | A | 3/1991 | DeSimone et al. |
| 5,004,624 | A | 4/1991 | Koschak et al. |
| 5,114,704 | A | 5/1992 | Spanier et al. |
| 5,256,697 | A | 10/1993 | Miller et al. |
| 5,294,641 | A | 3/1994 | Stanko |
| 5,339,771 | A | 8/1994 | Axelrod |
| 5,419,283 | A | 5/1995 | Leo |
| 5,532,010 | A | 7/1996 | Spanier et al. |
| 6,232,497 | B1 | 5/2001 | Pischel |
| 6,379,727 | B1 | 4/2002 | Addy |
| 6,417,231 | B1 | 7/2002 | Greenway et al. |
| 6,517,877 | B2 | 2/2003 | Gannon |
| 2004/0006139 | A1* | 1/2004 | Jager et al. ............ 514/554 |
| 2004/0054006 | A1 | 3/2004 | Kaddurah-Daouk et al. |
| 2004/0068006 | A1 | 4/2004 | Fink et al. |
| 2006/0025476 | A1* | 2/2006 | Antosh et al. ............ 514/546 |
| 2008/0161387 | A1 | 7/2008 | Gastner et al. |
| 2009/0098239 | A1 | 4/2009 | Gastner et al. |
| 2009/0182032 | A1* | 7/2009 | Zicker et al. ............ 514/440 |
| 2012/0004291 | A1* | 1/2012 | Yamka et al. ............ 514/440 |
| 2012/0289598 | A1* | 11/2012 | Yamka et al. ............ 514/557 |
| 2012/0309828 | A1* | 12/2012 | Yamka et al. ............ 514/557 |

FOREIGN PATENT DOCUMENTS

| | | |
|---|---|---|
| CN | 1224416 | 7/1999 |
| CN | 1350434 | 5/2002 |
| DE | 19836450 | 2/2000 |
| EA | 001388 | 2/2001 |
| GB | 2344996 | 6/2000 |
| JP | S57-175117 | 10/1982 |
| JP | H09-328423 | 12/1997 |
| JP | 2009-504766 | 2/2009 |
| JP | 2009-523827 | 6/2009 |
| RU | 2351153 | 4/2009 |
| WO | WO 90/06064 | 6/1990 |
| WO | WO 02/074301 | 9/2002 |
| WO | WO 02/081020 | 10/2002 |
| WO | WO 2006/113752 | 10/2006 |
| WO | WO 2010/083409 | 7/2010 |

OTHER PUBLICATIONS

Hu, 2009, "The Effects and Mechanism of Ethyl Pyruvate on Adjuvant-induced Arthritis of Rats," China Master's Theses Full-text Database (Medicine & Hygiene), 1:20-22.

Jinggui, 2005, "Progress in Anti-inflammatory Effects of Ethyl Pyruvate," Journal of Changzhi Medical College, 19(4).

Parvin et al., 1977, "Microdetermination of (-) Carnitine and Carnitine Acetyltransferases Activity," Analytical Biochemistry, 79:190-201.

Salahudeen et al., 1991, "Hydrogen peroxide-incuded renal injury. A protective role of pyruvate in vitro and in vivo." Journal of Clinical Investigation, 88(6):1886-1893 (XP-002374991).

(Continued)

*Primary Examiner* — Aradhana Sasan
(74) *Attorney, Agent, or Firm* — Thomas M. Hunter

(57) ABSTRACT

The invention encompasses compositions and methods for maintaining or promoting a healthy body composition in a companion animal, which comprises feeding the animal an edible composition comprising one or more pyruvate in an amount effective to maintain or promote the healthy body composition, wherein maintaining or promoting the healthy body composition comprises controlling the animal's weight, for example, loss of weight or body fat, or increased percentage of lean muscle mass.

8 Claims, No Drawings

(56) References Cited

OTHER PUBLICATIONS

International Search Report for International Application No. PCT/US2010/061868, mailed Apr. 5, 2011.
International Search Report for International Application No. PCT/US2010/061870, mailed Apr. 27, 2011.
International Search Report for International Application No. PCT/US2010/061875, mailed Mar. 31, 2011.
Yanos et al., 1994, "Hemodynamic effects of intravenous pyruvate in the intact, anesthetized dog," Critical Care Medicine, vol. 22(5):844-850 (XP-002628780). Abstract.
Roudebush et al., "An evidence-based review of the use of nutraceuticals and dietaty supplementation for the management of obese and overweight pets," JAVMA, Jun. 1, 2008, 232(11), 1646-1655.

* cited by examiner

COMPOSITIONS INCLUDING PYRUVATE FOR COMPANION ANIMALS AND METHODS OF USE THEREOF

CROSS-REFERENCE TO RELATED APPLICATIONS

This application is a national stage entry under 35 U.S.C. §371 of International Patent Application No. PCT/US2010/061875, filed 22 Dec. 2010, which claims priority to U.S. Provisional Patent Application No. 61/290,780 filed on 29 Dec. 2009, which are incorporated herein by reference.

BACKGROUND OF THE INVENTION

An important indicator of animal health is the body composition of the animal. An unhealthy diet and/or an unhealthy lifestyle can result in the animal having an unhealthy proportion of body fat, particularly in relation to lean muscle in the body. It is thought that a body fat amount in excess of 30% by weight indicates that the animal is unhealthy, particularly if the amount of body fat is in excess of 35% by weight.

Animals, particularly companion animals (e.g., dogs and cats), may weigh more than their ideal body weight. Having an excess of adipose tissue, these animals may be clinically diagnosed as, e.g., "fat", "overweight", or "obese" and, as such, are more likely to suffer from associated physical disorders such as arthritis, heart disease, respiratory disease, diabetes, bladder cancer, hypothyroidism, joint disease and/or pancreatitis.

Attempts to prevent or reduce the amount of excess adipose tissue on companion animals typically include dietary restriction and exercise. Indeed, many "low" or "reduced" calorie foods for overweight companion animals have been developed and are commercially available for the control of calorie intake, prevention of weight gain, or for the promotion of weight loss. One strategy in weight loss involves high protein diets with high protein to calorie ratios in order to reduce the amount of body fat in humans. A similar approach has been used in companion animal products. High protein diets have proven to be effective in weight loss in cats; however high protein foods have had mixed results when applied to canine weight management programs. Treatment strategies also include increasing the fiber and/or protein content while reducing the fat in the food. Depending on the fiber source, the fiber can induce satiety via gut distention or through feedback mechanisms (e.g., GLP-1). Fiber can be effective in reducing the digestibility of food resulting in a lower availability of high calorie nutrient components (i.e., fat and carbohydrates).

Generally, companion animals such as canines and felines weighing more than 15% of their ideal body weight are considered overweight or obese. Overweight animals generally have an excess of body adipose tissue. The most common cause of an animal being overweight is an over consumption of food that results in an excess intake of calories. However, there are other factors that can increase an animal's chances for being overweight, e.g., lifestyle, health, eating habits, breed, spaying, and neutering. Also, the incidence of animals becoming overweight generally increases with age due to a general decrease in metabolic rate and in physical activity. Surveys estimate that 25% of canines in the United States that visit veterinary clinics are fat to the point of being obese.

Losing weight or maintaining weight, particularly for a companion animal, is difficult. It is necessary to modulate the caloric intake of the animal. Modulating the amount of adipose tissue on a companion animal, including preventing an animal from becoming overweight or treating a fat animal to reduce the amount of adipose tissue on the animal, is also difficult. An effective way to prevent an animal from becoming fat or to reduce the amount of fat on an animal is with dietary restriction and exercise. However, it is often difficult to ensure compliance with diet and exercise programs.

Given the problems with current methods for losing weight or maintaining weight, there is a continuing need for new methods and compositions useful for maintaining or promoting a healthy body composition, wherein maintaining or promoting a healthy body composition comprises controlling the animal's weight, for example, loss of weight or body fat, or increased percentage of lean muscle mass, in a companion animal and, in particular, for food compositions effective in these conditions.

SUMMARY OF THE INVENTION

Accordingly, the inventors have developed edible compositions, including nutritionally complete dietary compositions for a companion animal, which include pyruvate to confer clinically beneficial properties with regard to maintaining or promoting a healthy body composition to such companion animal, wherein maintaining or promoting a healthy body composition may comprise controlling the animal's weight.

Another embodiment encompasses methods for maintaining or promoting a healthy body composition, wherein maintaining or promoting a healthy body composition comprises controlling the animal's weight, for example, loss of weight or body fat, or increased percentage of lean muscle mass in a companion animal, which includes feeding the animal an edible composition including one or more pyruvate in an amount effective to maintain or promote the healthy body composition.

DETAILED DESCRIPTION OF THE INVENTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

The invention generally encompasses companion animal edible compositions including one or more pyruvate in an amount effective to treat or prevent a disorder in the companion animal.

The invention additionally encompasses methods for the prevention, amelioration of symptoms of, or treatment of certain conditions, disorders and diseases in companion animals, for example, for promoting or maintaining healthy body compositions.

In one embodiment, maintaining or promoting a healthy body composition comprises controlling the animal's weight.

In another embodiment, the animal is overweight, obese, or has a tendency to be overweight or obese.

In another embodiment, the companion animal is a dog or cat.

In another embodiment, the pyruvate is present in an amount of up to about 20% by weight of the composition.

In another embodiment, the pyruvate is present in an amount of about 0.1% by weight to about 10% by weight of the composition In another embodiment, the pyruvate is in an amount of about 5% by weight of the composition.

In another embodiment, the pyruvate is in an amount of about 1% by weight of the composition.

In another embodiment, the pyruvate is in an amount of about 0.7% by weight of the composition.

In another embodiment, the composition further includes one or more proteins, fats, carbohydrates, fibers, and combinations thereof.

In another embodiment, the composition is a food, a nutritional diet, a supplement, an animal treat, or a toy.

In another embodiment, the edible composition is in the form of a moist food, dry food, supplement or treat.

Another embodiment of the invention encompasses methods for maintaining or promoting a healthy body composition in a companion animal, which includes feeding the animal an edible composition of the invention, which includes one or more pyruvate in an amount effective to maintain or promote the healthy body composition in such companion animal, wherein maintaining or promoting a healthy body composition comprises controlling the animal's weight.

It is contemplated that the invention described herein is not limited to the particular methodology, protocols, ingredients and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication, which might be used in connection with the invention.

As used herein and in the appended claims, the singular forms, and "the" include plural reference unless the context clearly dictates otherwise.

The term "antioxidant" means a substance that is capable of reacting with free radicals and neutralizing them. Illustrative examples of such substances include beta-carotene, selenium, coenzyme Q10 (ubiquinone), luetin, tocotrienols, soy isoflavones, S-adenosylmethionine, glutathione, taurine, N-acetylcysteine, vitamin E, vitamin C, lipoic acid and L-carnitine. Examples of foods containing useful levels of one or more antioxidants include but are not limited to, ginkgo bilboa, green tea, broccoli, citrus pulp, grape pomace, tomato pomace, carrot spinach, and a wide variety of fruit meals and vegetable meals. It will be understood by one of skill in the art that while units of antioxidants may be provided herein as "ppm", appropriate amounts of antioxidants may also be provided as "IU/kg" where appropriate and customary for a given antioxidant such as, e.g., Vitamin E.

The term "carbohydrate" as used herein includes polysaccharides (e.g., starches and dextrins) and sugars (e.g., sucrose, lactose, maltose, glucose, and fructose) that are metabolized for energy when hydrolyzed. Examples of carbohydrates suitable for inclusion in the compositions disclosed herein include but are not limited to, corn, grain sorghum, wheat, barley, and rice.

The term "cat" includes those cats which are companion animals known as domestic cats or house cats.

The term "companion animal" used in the present invention includes any non-human animal suitable for being kept as a pet by humans including a dog and a cat. All aspects of the present invention are preferably for the treatment of cats and/or dogs.

As used herein the term "compositions of the invention" refers to animal dietary food compositions including pyruvate. The compositions of the invention include pyruvate in an amount of about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 15%, or about 20% by weight. The compositions of the invention may maintain or promote a healthy body composition in a companion animal fed such compositions, wherein maintaining or promoting the healthy body composition comprises controlling the animal's weight, for example, loss of weight or body fat, or increased percentage of lean muscle mass The term "dog" includes those dogs which are companion animals such as *Canis familiaris*, working dogs and the like. The term dog is synonymous with the term canine.

As used herein, "an amount effective", "an effective amount", and like terms refer to that amount of a compound, material or composition as described herein that may be effective to achieve a particular biological result. Such effective activity may be achieved, for example, by administration of compositions of the present invention to an animal. An effective amount may be based on several factors, including an animal's ideal weight, the metabolizable energy of the composition, and frequency of feeding the animal compositions of the present invention, e.g., once, twice, or three times daily, and other compositions fed to the animal.

A "food" is a nutritionally complete diet for the intended recipient animal (e.g., domestic cat or domestic dog).

As used herein, an "ingredient" refers to any component of a composition.

As used herein, the terms "pyruvate" includes, but is not limited to, for example, pyruvic acid and salts and esters of pyruvic acid, including but not limited to: calcium pyruvate, sodium pyruvate, lithium pyruvate, potassium pyruvate, magnesium pyruvate, zinc pyruvate, manganese pyruvate and combinations thereof. The term "pyruvate" also includes certain pyruvate precursor molecules in the form of pyruvamides or pyruvyl-amino acids. The term pyruvyl-amino acids includes, pyruvyl-glycine, pyruvyl-glutamine, pyruvyl-lysine, pyruvyl-valine, pyruvyl-isoleucine, pyruvyl-phenylalanine, pyruvyl-proline and their amides, esters, salts and mixtures thereof. The term "pyruvate" also include derivatives of pyruvic acid such as ethyl pyruvate, propyl pyruvate, butyl pyruvate, carbmethoxymethyl pyruvate, carbethoxymethyl pyruvate, acetoxymethyl pyruvate, carbmethoxyethyl pyruvate, carbethoxylethyl pyruvate, methoxymethyl pyruvate and ethoxymethyl pyruvate. The term "pyruvate" also includes mixtures of any of the foregoing substances. In certain preferred embodiments, the pyruvate is calcium pyruvate.

The terms "sample" and "specimen" mean any animal tissue or fluid containing, e.g., polynucleotides, polypeptides, antibodies, metabolites, and the like, including cells and other tissue containing DNA and RNA. Examples include: blood, cartilage, connective, epithelial, lymphoid, muscle, nervous, sputum, and the like. A sample may be solid or liquid and may be DNA, RNA, cDNA, bodily fluids such as blood or urine, cells, cell preparations or soluble fractions or media aliquots thereof, chromosomes, organelles, and the like.

As used herein, "soluble fiber" refers to dietary fiber that attracts water during digestion and slows the rate of nutrient absorption and is typically found in, e.g., oat bran, seeds, beans, and certain fruits and vegetables such as beet pulp, guar gum, chicory root, psyllium, pectin, blueberry, cranberry, squash, apples, oats, beans, citrus, barley and peas. As used herein, the term encompasses any source of soluble fiber suitable for the compositions disclosed herein as would be evident to one of skill in the art.

As used herein, the term "supplement(s)" include but are not limited to, a feed used with another feed to improve nutritive balance or performance of the total. Supplements include but are not limited to, compositions that are fed undiluted as a supplement to other feeds, offered free choice with other parts of an animal's ration that are separately available, or diluted and mixed with an animal's regular feed to produce a complete feed. The AAFCO guidelines, for example, contain a discussion relating to supplements in the Official Publication of The Association of American Feed Control Officials, Inc. (AAFCO), Atlanta, Ga., 2005, or the National Research Council's *Nutrient Requirements of Dogs and Cats*, The National Academy Press, Washington, D.C., 2006.

Supplements may be in various foams including, for example, powders, liquids, syrups, pills, encapsulated compositions, and the like.

The term "nutrient" refers to a substance that provides nourishment. In some cases an ingredient may comprise more than one "nutrient," for example, a composition may comprise fish oil as an ingredient, the oil itself comprising important nutrients such as eicosapentaenoic acid and docosahexaenoic acid. The distinction in these terms is familiar to one of skill in the art.

As contemplated herein, the compositions of the present invention are meant to encompass nutritionally complete and balanced animal food compositions that additionally comprise pyruvate. A "nutritionally complete diet" is a diet that includes sufficient nutrients for maintenance of normal health of a healthy animal on the diet.

Nutritionally complete and balanced pet food compositions are familiar to one of skill in the art. For example, substances such as nutrients and ingredients suitable for nutritionally complete and balanced animal feed compositions, and recommended amounts thereof, may be found for example, in the Official Publication of The Association of American Feed Control Officials, Inc. (AAFCO), Atlanta, Ga., 2005, or the National Research Council's *Nutrient Requirements of Dogs and Cats*, The National Academy Press, Washington, D.C., 2006.

For example, a nutritionally complete and balanced pet food composition of the present invention may comprise: about 0 to about 90%, preferably about 5% to 60%, by weight of carbohydrates; about 5% to about 70%, preferably about 10% to about 60%, by weight of protein; about 2% to about 50%, preferably about 5% to about 40%, by weight of fat; about 0.1% to about 40%, preferably about 1% to about 11%, by weight of total dietary fiber; about 0 to about 15%, preferably about 2% to about 8%, by weight of vitamins and minerals, antioxidants, and other nutrients which support the nutritional needs of the animal; and about 0.1% to about 20% by weight of pyruvate.

One embodiment of the invention encompasses edible compositions for companion animals including one or more pyruvate.

Another embodiment encompasses methods for maintaining or promoting a healthy body composition, wherein maintaining or promoting a healthy body composition comprises controlling the animal's weight, for example, loss of weight or body fat, or increased percentage of lean muscle mass in a companion animal, which includes feeding the animal an edible composition including one or more pyruvate in an amount effective to maintain or promote the healthy body composition.

The compositions of the invention may include pyruvate in an amount effective to maintain or promote a healthy body composition, wherein maintaining or promoting a healthy body composition comprises controlling the animal's weight, for example, loss of weight or body fat, or increased percentage of lean muscle mass, in a companion animal.

Generally, the amount effective in the composition includes one or more pyruvate in an amount of up to about 20% by weight, up to about 18% by weight, up to about 16% by weight, up to about 14% by weight, up to about 12% by weight, up to about 10% by weight, up to about 9% by weight, up to about 8% by weight, up to about 7% by weight, up to about 6% by weight, up to about 5% by weight, up to about 4% by weight, up to about 3% by weight, up to about 2% by weight of the composition, or up to about 1% by weight. In certain embodiments, the one or more pyruvate is present in an amount of 0.5 to 1.0% by weight of the composition, and in other embodiments the one or more pyruvate is present in an amount of approximately 0.7% by weight of the composition.

The invention generally encompasses pet food compositions for a companion animal comprising an amount of protein, an amount of fat, an amount of carbohydrate, an amount of fiber and an effective amount of one or more pyruvate to maintain or promote a healthy body composition in a companion animal.

In certain embodiments, the effective amount of pyruvate is at least 0.1% by weight pyruvate. In other embodiments of the invention one or more pyruvate is present in a range of about 0.1% to about 20% by weight on a dry matter basis. In preferred embodiments the pyruvate is present in an amount of about 0.7% by weight on a dry matter basis.

In certain embodiments, the companion animal is a dog.

In certain embodiments, the companion animal is a cat.

In various embodiments, the companion animals of the invention are the domestic cat (Felis domesticus) or the domestic dog (Canis domesticus). Other companion animals include, fish, bird and horse.

In another embodiment, the animal is overweight, obese, or has a tendency to be overweight or obese.

In certain embodiments, the dietary food composition can be administered to an overweight or obese animal or to an animal that has a tendency to be overweight or obese.

The edible compositions, in addition to one or more pyruvate, may also include at least one component suitable for consumption by a companion animal including, but not limited to, fats, carbohydrates, proteins, fibers, nutritional balancing agents such as vitamins, minerals, and trace elements, and mixtures thereof. One of ordinary skill in the art can select the amount and type of food ingredients for a typical food based upon the dietary requirements of the animal, for example, the animal's species, age, size, weight, health, and function.

A "nutritionally complete diet" is a diet that includes sufficient nutrients for maintenance of normal health of a healthy animal on the diet. The methods of this invention utilize compositions that are not intended to be restricted by any specific listing of proteinaceous or fat ingredients or product form. The compositions can be prepared in, for example, a dry, canned, wet, or intermediate moisture form using conventional pet food processes.

The food composition can include up to about 100% of any particular food ingredient or can include a mixture of food ingredients in various proportions. In certain embodiments, the food composition includes a combination of food ingredients in amounts of about 0 wt. % to 50 wt. % fat, 0 wt. % to 75 wt. % carbohydrate, 0 wt. % to 95 wt. % protein, 0 wt. % to 40 wt. % dietary fiber, and 0 wt. % to 15 wt. % of one or more nutritional balancing agents.

In one illustrative embodiment, the composition may, for example, in addition to one or more pyruvate also include at least one of the following:
 (a) about 0% to about 75% carbohydrate;
 (b) about 2% to about 50% fat;
 (c) about 0% to about 40% dietary fiber, and
 (d) about 0% to about 15% of one or more nutritional balancing agents.

In certain embodiments, the fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice. In certain embodiments, protein may be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. Protein content of foods may be determined by any number of methods known by those of skill in the art, for example, as published by the Association of Official Analytical Chemists in *Official Methods of Analysis* ("OMA"). The amount of "crude protein" in a composition disclosed herein may be determined based on the amount of nitrogen in the composition according to methods familiar to one of skill in the art.

The compositions of the present invention may also include amino acids in amounts required to avoid deficiency and maintain health. These amounts and methods of measurement are known by those skilled in the art. For example, AAFCO provides recommended amounts of such ingredients for dogs and cats. Amino acids in the present compositions may be supplied by any number of sources, including crude protein, or addition of free amino acids to the composition.

Fat can be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. Fat content of foods may be determined by any number of methods known by those of skill in the art.

Carbohydrate may be supplied by any of a variety of sources known by those skilled in the art, including oat fiber, cellulose, peanut hulls, beet pulp, parboiled rice, corn starch, corn gluten meal, and any combination of those sources. Grains supplying carbohydrate include, but are not limited to, wheat, corn, barley, and rice. Carbohydrate content of foods may be determined by any number of methods known by those of skill in the art. Generally, carbohydrate percentage may be calculated as nitrogen free extract ("NFE"), which may be calculated as follows: NFE=100%−moisture %−protein %−fat %−ash %−crude fiber %.

As used herein, "fiber blend" includes a combination of soluble and insoluble fiber at a level that is between 1-5% total dietary fiber on a dry matter basis. The sources of the fiber can be combinations of cellulose, hemicelluloses, resistant starches, or oligosaccharides such as galactooligosaccharides, xylooligosaccharides, or fructooligosaccharides.

Dietary fiber refers to components of a plant that are resistant to digestion by an animal's digestive enzymes. Dietary fiber components of foods may be determined by any number of methods known by those of skill in the art, such as those published by the OMA. Dietary fiber includes soluble and insoluble fibers.

Soluble fiber are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, or peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber. Soluble and insoluble fiber content of foods may be determined by any number of methods known by those of skill in the art. Crude fiber includes indigestible components contained in cell walls and cell contents of plants such as grains, e.g., hulls of grains such as rice, corn, and beans. Crude fiber content of foods may be determined by any number of methods known by those of skill in the art.

In certain embodiments, the fiber food ingredient is obtained from a variety of sources such as vegetable fiber sources, for example, cellulose, beet pulp, peanut hulls, and soy fiber.

Metabolizable energy (ME) of a diet is the energy available to an animal upon consumption of the diet after subtracting the energy excreted in feces, urine, and combustible gases. Metabolizable energy values may be determined by methods known by those skilled in the art, such as detailed in the Official Publication of The Association of American Feed Control Officials, Inc. or the National Research Council's *Nutrient Requirements of Dogs and Cats*, The National Academy Press, Washington, D.C., 2006.

"Ash" consists of compounds that are not organic or water, generally produced by combustion of biological materials. Ash may be determined by any number of methods known by those of skill in the art.

Carnitine, or L-carnitine, is a vitamin-like compound synthesized in the body from lysine and methionine. Carnitine may be naturally present in ingredients of the present invention, or carnitine may be added to the compositions.

The compositions of the present invention also may contain one or more minerals and/or trace elements, e.g., calcium, phosphorus, sodium, potassium, magnesium, manganese, copper, zinc, or iron salts. One particular trace element is manganese. Manganese is essential to a host of enzymes as a cofactor, which may regulate the metabolism of foods, including proteins, fats, and carbohydrates. Such enzymes may include oxidoreductases, transferases, hydrolases, lyases, isomerases, ligases, lectins, and integrins. Manganese also affects bone development and neurological function. Manganese may be naturally present in the components of the compositions, or it may be added to compositions. Methods of measuring manganese content in a composition are well known to those of skill in the art.

The compositions of the present invention may also include vitamins and minerals in amounts required to avoid deficiency and maintain health. These amounts and methods of measurement are known by those skilled in the art. For example, AAFCO provides recommended amounts of such ingredients for dogs and cats. As contemplated herein, useful vitamins may include, but are not limited to, vitamin A, vitamin $B_1$, vitamin $B_2$, vitamin $B_6$, vitamin $B_{12}$, vitamin C, vitamin D, vitamin E, vitamin H (biotin), vitamin K, folic acid, inositol, niacin, and pantothenic acid.

In certain embodiments, the nutritional balancing agents are obtained from a variety of sources known to skilled artisans, for example, vitamin and mineral supplements and food ingredients. Vitamins and minerals can be included in amounts required to avoid deficiency and maintain health. These amounts are readily available in the art. The Association of American Feed Control Officials, Inc. provides recommended amounts of such nutrients for dogs and cats. Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

In certain embodiments, the food compositions may contain additional ingredients such as fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of animal; the animal's age, body weight, general health, sex, and diet; the animal's consumption rate; the type of disease or condition being treated; and the like. Therefore, the component and ingredient amounts may vary widely and may deviate from the preferred proportions described herein.

The invention encompasses pet food compositions or supplements wherein one or more pyruvate is present in an effective amount to prevent, ameliorate one or more symptoms of, or treat, a condition in a companion animal. The effective amount of one or more pyruvate may vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the nutritional supplement or nutritionally complete diet, and the severity of the illness or symptom. It is within the skill of the person of ordinary skill in the art to account for these factors.

The food composition may further contain other ingredients such as corn, poultry meal, grease, palatability enhancers, potassium chloride, iodized salt, calcium carbonate, choline chloride, mineral premix, preservative, vitamin premix. The food may contain protein. The protein may be animal protein. Animal protein may be part of the total protein. Animal protein may be 50%, 70%, 80%, 90%, 95%, 99% or 100% of the total protein. The food may contain antioxidants, such as vitamin E. Antioxidant may be present in between about 0.0001 U/g and 3.0 U/g food, such as, e.g., 0.18 U/g. The food may contain eicosapentaenoic acid (EPA) at between 1% by weight and 5% weight. Fatty acids may also be included such as n-3 and n-6 fatty acids. Fatty acids may be present in about 0.05% to 5% by weight. n-3 fatty acids may be present in about 0.0001% to 2%. n-6 fatty acids may be present in about 0.5% to 5% by weight. The food may contain fiber, such as crude fiber. Fiber may be present in between 0.001% and 10% by weight.

The effective amount of the nutritional supplement will vary depending on such factors as the patient being treated, the particular mode of administration, the activity of the particular active ingredients employed, the age, body weight, general health, sex and diet of the patient, time of administration, rate of excretion, the particular combination of ingredients employed, the total content of the main ingredient of the nutritional supplement, and the severity of the illness or symptom. It is within the skill of the person of ordinary skill in the art to account for these factors.

The pyruvate-containing dietary foods or supplements of the present invention may be formulated using a safe and effective amount of one or more pyruvate as discussed herein to provide one or more of the beneficial effects of the invention described herein, and one or more of the optional ingredients which may be obtained from slippery elm or green tea, as well as one or more of the additional optional ingredients described below. The nutritional supplement of the present invention may also be formulated with a pharmaceutically acceptable carrier.

Other materials, which may optionally be included in the nutritional supplement of the present invention include inositol, other B-complex vitamins, and anti-inflammatories. Also, ingredients such as sweeteners, flavorants, coloring agents, dyes, preservatives, emulsifying agents, suspending agents, melting agents, excipients, and solvents or diluents such as water, ethanol, propylene glycol, glycerin and various combinations thereof, may be included in the pyruvate-containing foods or supplements of the present invention.

The optional sweeteners, which may be used in the pyruvate-containing foods or supplements of the present invention include, but are not limited to, saccharin, aspartame, cyclamates, acesulfame K, neohesperidin dihydrochalcone, other sweeteners, and mixtures thereof, which may be added to the carrier in amounts sufficiently low so as not to chemically interact with the main ingredients of the nutritional supplement.

The optional flavorants which may be used in the pyruvate-containing foods or supplements of the present invention include, but are not limited to, peppermint, peppermint-menthol, eucalyptol wintergreen, licorice, clove, cinnamon, spearmint, cherry, lemon, orange lime, menthol and various combinations thereof.

Such additives are present in amounts that do not impair the purpose and effect provided by the invention. Examples of additives include, for example, substances with a stabilizing effect, processing aids, substances that enhance palatability, coloring substances, and substances that provide nutritional benefits.

Stabilizing substances include, for example, substances that tend to increase the shelf life of the composition. Potentially suitable examples of such substances include, for example, preservatives, antioxidants, synergists and sequesterants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Additives for coloring, palatability, and nutritional purposes include, for example, colorants (e.g., iron oxide, such as the red, yellow, or brown forms); sodium chloride, potassium citrate, potassium chloride, and other edible salts; vitamins; minerals; and flavoring. Such additives are known in the art. See, e.g., U.S. Pat. No. 3,202,514. See also, U.S. Pat. No. 4,997,671. Flavorants include, for example, dairy product flavorants (e.g., milk or cheese), meat flavorants (e.g., bacon, liver, beef, poultry, or fish), oleoresin, pinacol, and the various flavorants identified in the trade by a FEMA (Flavor Extract Manufacturers Association) number. Flavorants help provide additional palatability, and are known in the art. See, e.g., U.S. Pat. No. 4,997,672. See also, U.S. Pat. Nos. 5,004,624, 5,114,704, 5,532,010, and 6,379,727. The concentration of such additives in the composition typically may be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly where such additives are primarily nutritional balancing agents) is from about 0% to about 1.0% by weight.

The composition of the invention may include one or more additional ingredients to prevent or treat one or more diseases or conditions. The component in the diet, which accomplishes this, may be an antioxidant or mixture thereof. An antioxidant is a material that quenches a free radical. Examples of such materials include foods such as Ginkgo Biloba, citrus pulp, grape pomace, tomato pomace, carrot and spinach, all preferably dried as well as various other materials such as beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, l-carnitine and the like. Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The d form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form such as liquid, semisolid, solid and heat stable form. L-carnitine can be administered in the diet and various derivatives of carnitine such as the salts such as the hydrochloride, fumarate and succinates, as well as acetylated carnitine, and the like can be used.

As contemplated herein, functional ingredients and nutrients for use in the present invention include walnut oil, sesame oil, sunflower oil, capsibiol-T, pomegranate, magnolia, lipoic acid, vitamin C, ginger, green and black tea, optionally together with an optimal fiber blend of soluble and insoluble fibers. Juices, extracts, pulp or other forms of formulations of said ingredients are included.

In various embodiments, the pet food composition can further include corn, poultry meal, palatability enhancers, potassium chloride, iodized salt, calcium carbonate, choline chloride, minerals, mineral premix, preservatives, vitamins, and mixtures thereof. In certain embodiments, the dietary food composition may further include L-tryptophan. The quantities administered in the diet, all as wt % (dry matter basis) of the diet, are calculated as the active material, per se, that is measured as free material. The maximum amounts employed should not bring about toxicity. At least about 100 ppm or at least about 150 ppm of Vitamin E can be used. A preferred range of 500 to 1,000 ppm can be employed. Although not necessary, a maximum of about 2000 ppm or about 1500 ppm is generally not exceeded. With respect to Vitamin C at least about 50 ppm is used, desirably at least about 75 ppm and more desirably at least about 100 ppm. A non-toxic maximum can be employed. The quantity of lipoic acid can vary from at least about 25, desirably at least about 50 ppm, more desirably about 100 ppm. Maximum quantities can vary from 100 ppm to 600 ppm or to an amount which remains non-toxic to the pet. A preferred range is from 100 ppm to 200 ppm. For l-carnitine about 50 ppm, desirably about 200 ppm, more desirably about 300 ppm for canines are a useful minimum. For felines, slightly higher minimums of l-carnitine can be employed such as about 100 ppm, 200 ppm, and 500 ppm. A non-toxic maximum quantity can be employed, for example, less than about 5,000 ppm. For canines, lower quantities can be employed, for example, less than about 5,000 ppm. For canines, a preferred range is 200 ppm to 400 ppm. For felines, a preferred range is 400 ppm to 600 ppm. Beta-carotene at 1-15 ppm can be employed. Selenium at 0.1 up to 5 ppm can be employed. Lutein at least about 5 ppm can be employed. Tocotrienols at least about 25 ppm can be employed. Coenzyme Q10 at least about 25 ppm can be employed. S-adenosylmethionine at least about 50 ppm can be employed. Taurine at least about 1000 ppm can be employed. Soy isoflavones at least about 25 ppm can be used. N-acetylcysteine at least about 50 ppm can be used. Glutathione at least about 50 ppm can be used. Gingko Biloba at least 50 ppm of extract can be used.

In various embodiments, the pyruvate may be added to the animal's food. In various embodiments, the pyruvate may be added to the animal's food by a compounder or manufacturer at a site or by an animal's caregiver prior to feeding the animal. In various embodiments, the pyruvate may be added during the processing of an animal's food, such as during and/or after mixing of other components of the composition that is then packaged and made available to consumers. Such processing may include extrusion, canning, baking, and the like or any other method or process of producing pet foods that is known in the art. In various embodiments, the pyruvate may be contributed by a natural source like an animal or plant component or the pyruvate may be contributed by a synthetically derived source or the pyruvate may be contributed by a mixture of natural and synthetic sources.

The edible compositions of the invention may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, for example, direct steam injection or using a vessel fitted with a heat exchanger. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. The compositions of the present invention can be added to the food compositions before, during, or after preparation.

Food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavours, fats, oils, powders, and the like. Kibble also can be made from the dough using a baking process, rather than extrusion, wherein the dough is placed into a mold before dry-heat processing.

In preparing a composition for use with the methods of the present invention, any ingredient (e.g., fish oil) generally may, for example, be incorporated into the composition during the processing of the formulation, such as during and/or after mixing of other components of the composition. Distribution of these components into the composition can be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added.

Methods of the present invention include utilizing compositions that can be prepared in a dry form using conventional processes. In one embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

The compositions may also be designed to be easier to chew. Canine and feline foods are typically formulated based on life stage (age), size, body composition, and breed. In the methods of this invention, some embodiments of the compositions address specific nutritional differences between senior regular or small breed dogs, large breed dogs, and cats.

All percentages expressed herein are on a weight by dry matter basis unless specifically stated otherwise.

In one embodiment, the compositions are in the foam of a companion animal food composition or pet food.

Foods of any consistency or moisture content are contemplated, e.g., the compositions of the present invention may be a moist, semi-moist, or dry animal food composition. "Moist" food refers to food that has a moisture content of 60 to 90% or greater. "Dry" food refers to compositions with 3 to 11% moisture content and is often manufactured in the form of small bits or kibbles. "Semi-moist" refers to compositions with 25-35% moisture content. Also contemplated herein are compositions that may comprise components of various consistency as well as components that may include more than one consistency, for example, soft, chewy meat-like particles as well as kibble having an outer cereal component and an inner cream component as described in, e.g., U.S. Pat. No. 6,517,877.

The edible composition can be a liquid or a solid food. When the composition is a liquid, the pyruvate can be admixed with other components. Where the composition is solid, the pyruvate may be coated on the composition, incorporated into the composition, or both.

In certain embodiments, the edible composition can be a supplement. Supplements include, for example, a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. AAFCO, for example, provides a discussion relating to supplements in the Official Publication of The Association of American Feed Control Officials, Inc. (2009). Supplements may be in various forms including, for example, powders, liquids, syrups, pills, encapsulated compositions, and the like.

In certain embodiments, the edible composition can be a treat. Treats include compositions that are given to an animal to entice the animal to eat during a non-meal time, for example, dog bones for canines. Treats may be nutritional wherein the composition includes one or more nutrients and may have a food-like composition. Non-nutritional treats encompass any other treats that are non-toxic. The composition or components are coated onto the treat, incorporated into the treat, or both. Treats of the invention can be prepared by an extrusion or baking process similar to those used for dry food. Other processes also may be used to either coat the composition on the exterior of existing treat forms or inject the composition into an existing treat form.

In certain embodiments, the edible composition can be a toy. Toys include chewable toys such as artificial bones. The at least one pyruvate can form a coating on the surface of the toy or on the surface of a component of the toy, be incorporated partially or fully throughout the toy, or both. In one embodiment, the one or more pyruvate is orally accessible by the intended user. There are a wide range of suitable toys currently marketed, for example, U.S. Pat. Nos. 5,339,771, 5,419,283, and references disclosed therein. This invention provides both partially consumable toys, for example, toys including plastic components, and fully consumable toys, for example, rawhides and various artificial bones. The invention preferably provides toys for use by a dog or a cat.

The invention also encompasses methods of preventing, ameliorating one or more symptoms of, or treating certain disorders by administering a therapeutically or prophylactically effective amount of a composition including one or more pyruvate to a companion animal in need thereof.

In one embodiment the composition providing a therapeutically or prophylactically effective amount of one or more pyruvate is administered in a nutritionally complete dietary composition.

Another embodiment encompasses methods for maintaining or promoting a healthy body composition, for example, loss of weight or body fat, or increased percentage of lean muscle mass, in a companion animal, which includes feeding the animal an edible composition including one or more pyruvate in an amount effective to promote or maintain the healthy body composition.

In another embodiment, the invention encompasses the use of an edible composition including one or more pyruvate for the manufacture of a medicament for maintaining or promoting a healthy body composition in a companion animal. In certain embodiments, the invention encompasses administering the composition including one or more pyruvate to overweight or obese companion animals. The composition may also be fed to companion animals that are healthy in order to maintain a healthy body composition. The invention is based upon the discovery that the presence of one or more pyruvate in an animal's diet enhances or improves weight promotion and maintenance.

Specific Embodiments of the Invention

The invention is further described in the following examples. The examples are merely illustrative and do not in any way limit the scope of the invention as described and claimed. This invention can be further illustrated by the following examples of preferred embodiments thereof, although it will be understood that these examples are included merely for purposes of illustration and are not intended to limit the scope of the invention unless otherwise specifically indicated.

EXAMPLES

Example 1

Effect of Pyruvate on Body Composition in Canine and Feline Studies Materials and Methods 28 cats were fed a control food for 28 days prior to the start of the study. At day 0, cats were allotted to one of two foods, the control food or the control food+pyruvate. Cats were fed the experimental foods for 45 days. At day 0 and 45, blood was harvested to determine chemistry profile and Dual energy x-ray absorptiometry (DEXA) was performed to determine changes in body composition.

40 dogs were fed a control food for 28 days prior to start of the study. At day 0, dogs were allotted to one of three experimental foods, control+fish oil, control+pyruvate, or control+fish oil and pyruvate. Dogs were fed the experimental foods for 45 days. At day 0 and 45, blood was harvested to determine chemistry profile and DEXA was performed to determine changes in body composition.

TABLE 1

Ingredients Used to Make Feline and Canine Control Foods

| Ingredient Order | Feline Control Food | Canine Control Food |
| --- | --- | --- |
| 1 | Corn Gluten Meal | Corn |
| 2 | Corn | Poultry meal |

TABLE 1-continued

Ingredients Used to Make Feline and Canine Control Foods

| Ingredient Order | Feline Control Food | Canine Control Food |
| --- | --- | --- |
| 3 | Poultry Meal | Corn Gluten Meal |
| 4 | Cellulose | Cellulose |
| 5 | Beet Pulp | Soybean meal run |
| 6 | Soybean oil | Beet Pulp |
| 7 | Pal Enhancer 1 | Pal Enhancer |
| 8 | Pal Enhancer 2 | Soybean oil |
| 9 | L-Lysine | Potassium Citrate |
| 10 | Potassium Chloride | DL-methionine |
| 11 | Calcium Sulfate | Pal enhancer 2 |
| 12 | L-carnitine | L-lysine |
| 13 | Choline Chloride | L-carnitine |
| 14 | DL-Methionine | Vitamin E |
| 15 | Vitamin E | Salt |
| 16 | Glycerol Monosaturate | Choline chloride |
| 17 | Potassium Citrate | Vitamin premix |
| 18 | Vitamin Premix | Mineral premix |
| 19 | Taurine | L-lysine |
| 20 | Salt | Taurine |
| 21 | L-Arginine | — |
| 22 | Mineral Premix | — |

* Calcium pyruvate was added to these foods at 1% at the expense of corn for the experimental foods.

TABLE 2

Feline Pyruvate Study Body Composition Day 0[a,b]

| Item | Feline control | Feline control + pyruvate | SE | Treatment |
| --- | --- | --- | --- | --- |
| Body composition | | | | |
| Bone mineral content, g | 117 | 118 | 11.96 | 0.91 |
| Percent BMC, % | 3.18 | 3.24 | 0.176 | 0.76 |
| Bone mineral density, g | 0.61 | 0.61 | 0.017 | 0.99 |
| Lean, g | 2842 | 2888 | 226.25 | 0.84 |
| Percent lean, % | 78.0 | 79.5 | 2.490 | 0.55 |
| Percent fat, % | 18.8 | 17.2 | 2.590 | 0.55 |
| Total fat | 735 | 663 | 143.2 | 0.62 |
| Total weight, g | 3693 | 3670 | 347.5 | 0.95 |

[a] Cats were fed maintenance food for 28 days prior to day 0.
[b] Cats were offered food ad libitum of 100 grams per day.

TABLE 3

Feline Pyruvate Study Body Composition and Food Intake Day 45[a,b,c,d]

| Item | Feline control | Feline control + pyruvate | SE | Treatment |
| --- | --- | --- | --- | --- |
| Daily food intake, g | 51.5 | 44.7 | 5.25 | 0.21 |
| Body composition | | | | |
| Bone mineral content, g | 114 | 113 | 1.025 | 0.20 |
| Percent BMC, % | 3.13 | 3.39 | 0.065 | 0.001 |
| Bone mineral density, g | 0.60 | 0.60 | 0.003 | 0.64 |
| Lean, g | 2799 | 2709 | 36.78 | 0.02 |
| Percent lean, % | 77.57 | 81.95 | 1.083 | 0.001 |
| Percent fat, % | 19.32 | 15.24 | 1.019 | 0.001 |
| Total fat | 737 | 551 | 46.82 | 0.001 |
| Total weight, g | 3648 | 3360 | 69.26 | 0.001 |
| Change in fat | 32.07 | −147.2 | 47.87 | 0.001 |
| Change in lean | −63 | −157 | 36.77 | 0.02 |
| Change in weight | −34.6 | −322.5 | 68.48 | 0.001 |

[a] 15 cats fed feline control and 13 cats fed feline control + 1% calcium pyruvate
[b] Cats were fed the feline control for 28 days prior to starting the test.
[c] Cats were offered food ad libitum of 100 grams per day.
[d] Day 0 was used as a covariate in the analysis.

Cats fed the control+pyruvate food increased lean muscle mass percent, decreased body fat percent and lost weight.

TABLE 4

Canine Pyruvate Study Body Composition Day 0[a,b]

| Item | A Canine control + fish oil | B Canine control + pyruvate | C Canine control + pyruvate/fish oil | SE | Probability A vs B | A vs C | B vs C |
|---|---|---|---|---|---|---|---|
| Body composition | | | | | | | |
| Bone mineral content, g | 476 | 489 | 500 | 43.3 | 0.76 | 0.59 | 0.81 |
| Percent BMC, % | 3.3 | 3.4 | 3.4 | 0.136 | 0.63 | 0.40 | 0.70 |
| Bone mineral density, g | 0.846 | 0.850 | 0.857 | 0.021 | 0.82 | 0.60 | 0.76 |
| Lean, g | 9886 | 10080 | 10166 | 805.5 | 0.81 | 0.73 | 0.91 |
| Percent lean, % | 68.3 | 69.7 | 70.8 | 3.23 | 0.64 | 0.43 | 0.73 |
| Percent fat, % | 28.4 | 26.9 | 25.7 | 3.32 | 0.64 | 0.42 | 0.72 |
| Total fat | 4210 | 3974 | 3861 | 672.5 | 0.61 | 0.87 | 0.98 |
| Total weight, kg | 14.6 | 14.5 | 14.5 | 1.2 | 0.98 | 0.97 | 0.99 |

[a]Dogs were fed maintenance food for 28 days prior to day 0.
[b]All dogs were offered food ad libitum of 400 grams per day.

TABLE 5

Canine Pyruvate Study Body Composition and Food Intake Day 45[a,b,c]

| Item | A Canine control + Fish oil | B Canine control + pyruvate | C Canine control + Fish oil/pyruvate | SE | Probability A vs B | A vs C | B vs C |
|---|---|---|---|---|---|---|---|
| Daily food intake, g | 313 | 341 | 339 | 21.53 | 0.19 | 0.24 | 0.90 |
| Body composition | | | | | | | |
| Bone mineral content, g | 487 | 488 | 485 | 4.255 | 0.90 | 0.54 | 0.45 |
| Percent BMC, % | 3.38 | 3.45 | 3.41 | 0.042 | 0.11 | 0.42 | 0.43 |
| Bone mineral density, g | 0.845 | 0.851 | 0.844 | 0.003 | 0.06 | 0.770 | 0.03 |
| Lean, g | 10218 | 10289 | 10092 | 148.86 | 0.63 | 0.41 | 0.19 |
| Percent lean, % | 71.4 | 73.3 | 71.6 | 0.917 | 0.04 | 0.86 | 0.06 |
| Percent fat, % | 25.22 | 23.30 | 25.02 | 0.930 | 0.04 | 0.83 | 0.07 |
| Total fat | 3717 | 3487 | 3626 | 146.4 | 0.03 | 0.33 | 0.21 |
| Total weight, g | 14.4 | 14.2 | 14.2 | 0.17 | 0.16 | 0.16 | 0.98 |
| Change in fat | −322 | −623 | −423 | 167.6 | 0.08 | 0.55 | 0.23 |
| Change in lean | 177 | 243 | 44 | 148.2 | 0.65 | 0.38 | 0.18 |
| Change in weight | −146 | −380 | −383 | 175.9 | 0.18 | 0.19 | 0.99 |

[a]13 dogs fed canine control + fish oil, 13 dogs fed Canine control + 1% calcium pyruvate and 13 dogs fed Canine control + pyruvate and fish oil
[b]Dogs were fed canine control for 28 days prior to starting the test.
[c]All dogs were offered food ad libitum of 400 grams per day.
[d]Day 0 was used as a covariate in the analysis.

Dogs fed the control+pyruvate food increased lean muscle mass percent, decreased body fat percent, and lost weight.

What is claimed is:

1. A method for maintaining or promoting a healthy body composition in a companion animal which is a dog or cat, which comprises feeding the animal an edible composition comprising for a dog or cat comprising one or more pyruvate in an amount effective to maintain or promote the healthy body composition, wherein the one or more pyruvate is present in the composition in an amount of about 3% to about 6% by weight of the composition,
wherein said one or more pyruvate is calcium pyruvate.

2. The method of claim 1, wherein the one or more pyruvate is present in the composition in an amount of about 3% to about 4%, or about 5%, or about 6%.

3. The method of claim 1 wherein maintaining or promoting the healthy body composition comprises controlling the animal's weight.

4. The method of claim 1 wherein the animal is overweight, obese, or has a tendency to be overweight or obese.

5. The method of claim 1, wherein the composition further comprises a component selected from the group consisting of protein, fat, carbohydrate, fiber, and combinations thereof.

6. The method of claim 1, wherein the composition is a food, a nutritional diet, a supplement, an animal treat, or a toy.

7. The method of claim 1, wherein the companion animal is a dog.

8. The method of claim 1, wherein the companion animal is a cat.

* * * * *